(12) United States Patent
Toyota et al.

(10) Patent No.: US 12,402,795 B2
(45) Date of Patent: Sep. 2, 2025

(54) BODY TEMPERATURE ESTIMATION DEVICE

(71) Applicant: Nippon Telegraph and Telephone Corporation, Tokyo (JP)

(72) Inventors: Shin Toyota, Tokyo (JP); Kazuyoshi Ono, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 170 days.

(21) Appl. No.: 18/256,181

(22) PCT Filed: Dec. 9, 2020

(86) PCT No.: PCT/JP2020/045791
§ 371 (c)(1),
(2) Date: Jun. 6, 2023

(87) PCT Pub. No.: WO2022/123668
PCT Pub. Date: Jun. 16, 2022

(65) Prior Publication Data
US 2024/0032800 A1 Feb. 1, 2024

(51) Int. Cl.
*A61B 5/01* (2006.01)
*A61B 5/00* (2006.01)

(52) U.S. Cl.
CPC .............. *A61B 5/01* (2013.01); *A61B 5/0075* (2013.01)

(58) Field of Classification Search
CPC ......... A61B 5/01; A61B 5/0075; A61B 5/015; G01J 5/48
See application file for complete search history.

(56) References Cited

U.S. PATENT DOCUMENTS

| | | | |
|---|---|---|---|
| 2009/0296044 A1* | 12/2009 | Howell | G02C 11/10 351/158 |
| 2015/0148681 A1* | 5/2015 | Abreu | A61B 5/6821 600/474 |
| 2019/0212214 A1* | 7/2019 | Liang | A61B 5/0075 |

OTHER PUBLICATIONS

Ota et al., "Environmental science for society: introduction of a case of body surface temperature measurement by infrared thermography from the viewpoint of influenza spread prevention," NEC Technical Journal, vol. 62, No. 3, 2009, pp. 87-91. As discussed in the specification.

* cited by examiner

*Primary Examiner* — John D Li
(74) *Attorney, Agent, or Firm* — Slater Matsil, LLP

(57) ABSTRACT

An estimator estimates the body temperature of a subject from the temperatures of the inner corners of the eyes in the temperature information obtained from a measurement result of an infrared sensor. The infrared sensor two-dimensionally measures the distribution of infrared rays radiated from the surface of the face of the subject including the inner corners of the eyes of the subject, and the estimator obtains a temperature distribution from the data of the distribution of the light intensity of the infrared rays and identifies the inner corners of the eyes from the obtained temperature distribution to estimate the temperatures of the identified inner corners of the eyes as the body temperature. A corrector corrects the body temperature estimated by the estimator by the difference between the temperatures of the inner corners of the left and right eyes in the measurement result of the infrared sensor.

7 Claims, 6 Drawing Sheets

BODY TEMPERATURE ESTIMATION DEVICE

CROSS-REFERENCE TO RELATED APPLICATIONS

This application is a national phase entry of PCT Application No. PCT/JP2020/045791, filed on Dec. 9, 2020, which application is hereby incorporated herein by reference.

TECHNICAL FIELD

The present invention relates to a body temperature estimation device.

BACKGROUND

There has been known a body temperature measuring device which captures a thermal image of a subject using an infrared thermography (thermal imaging sensor) and estimates a body temperature such as a deep body temperature of the subject from the obtained thermal image. This body temperature measuring device is a convenient measuring device due to its ability to measure the body temperature of a subject instantaneously in a non-contact manner.

All objects radiate energy at a certain wavelength due to the vibration or rotation of atoms and molecules at or above absolute zero (0K: −273.15° C.). The infrared thermography receives energy radiated from an object and obtains the temperature of the object based on the Stefan-Boltzmann's law to image the object as a two-dimensional temperature distribution.

Infrared thermography having such a feature is widely applied not only in the electric and electronic fields but also in the quality control of industrial products, plant maintenance, structure diagnosis, and security monitoring. As described in NPL 1, one application example of this technique is a countermeasure against a pandemic, wherein the spread of infection can be prevented by sensing a fever caused by an infectious disease such as influenza by installing the technique at a gate of an airport or the like.

However, in a case where the infrared thermography is used for the body temperature measurement in a situation where the line of flow is not fixed, such as in measures against heat stroke during exercise, there is a possibility that a body temperature rise of the subject cannot be detected because the subject is moving. Although there is a technique for monitoring the body temperature of a subject during exercise by using a contact-type temperature sensor, such technology may cause not only psychological discomfort but also physical damage such as eczema in some people due to the reduced ventilation of the contact area and the feel of the temperature sensor on the skin.

CITATION LIST

Non Patent Literature

NPL 1 Jiro Ota, Eri Hamada, "Environmental science for society: introduction of a case of body surface temperature measurement by infrared thermography from the viewpoint of influenza spread prevention," NEC Technical Journal, vol. 62, No. 3, pages 87-91, 2009.

SUMMARY

Technical Problem

As described above, in a case where the infrared thermography is used to measure the body temperature of a subject in a situation where the line of flow is not fixed, such as when the subject is doing exercise, there is a problem that a change in the body temperature such as a rise in the body temperature of the subject cannot be measured.

Embodiments of the present invention were made to solve the problems described above, and an object thereof is to enable measurement of changes in body temperature of a subject even in a situation where the line of flow is not fixed.

Solution to Problem

A body temperature estimation device according to embodiments of the present invention includes: a holding mechanism that is mounted on the head of a subject; an infrared sensor that is provided in the holding mechanism and two-dimensionally measures a distribution of infrared rays emitted from a surface of the face of the subject including inner corners of the eyes of the subject; an estimation unit that estimates a body temperature of the subject from temperatures of the inner corners of the eyes in a measurement result from the infrared sensor; a correction unit that corrects the body temperature estimated by the estimation unit, based on a difference between a temperature of the inner corner of the left eye and a temperature of the inner corner of the right eye in the measurement result from the infrared sensor; and a display control unit that displays the body temperature corrected by the correction unit on a display unit.

Advantageous Effects of Embodiments of the Invention

As described above, according to embodiments of the present invention, the infrared sensor for measuring infrared rays emitted from the surface of the face of the subject is provided in the holding mechanism, the body temperature of the subject is estimated from the temperatures of the inner corners of the eyes in the measurement result, and the estimation result is corrected by the difference between the temperature of the inner corner of the left eye and the temperature of the inner corner of the right eye. Therefore, even in a situation where the line of flow is not fixed, changes in body temperature of the subject can be measured.

DETAILED DESCRIPTION OF ILLUSTRATIVE EMBODIMENTS

Figure 1:
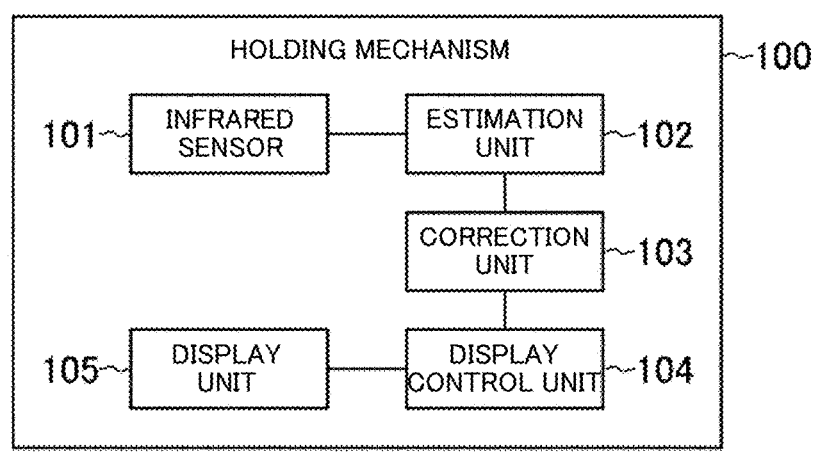
FIG. 1 is a configuration diagram showing a configuration of a body temperature estimation device according to an embodiment of the present invention.

A body temperature estimation device according to an embodiment of the present invention will be described hereinafter with reference to FIGS. 1 and 2. The body temperature estimation device includes a holding mechanism 100, an infrared sensor 101, an estimation unit 102, a correction unit 103, a display control unit 104 and a display unit 105.

The holding mechanism 100 is mounted on the head of a subject. The holding mechanism 100 can be constituted by, for example, a face guard or a mouth shield. The infrared sensor 101 is provided in the holding mechanism 100 and measures infrared rays radiated from the surface of the face of the subject. Examples of the infrared sensor 101 include a thermal image sensor such as an infrared thermography camera for two-dimensionally measuring the distribution of infrared rays radiated from the surface of the face including the inner corners of the eyes of the subject.

The estimation unit 102 estimates the body temperature of the subject from the temperatures of the inner corners of the eyes in temperature information obtained from a measurement result of the infrared sensor 101. For example, the temperature is calculated from data of the infrared light intensity measured by the infrared sensor 101, and the body temperature of the subject is estimated from the temperatures of the inner corners of the eyes in the calculated temperature. The infrared sensor 101 two-dimensionally measures the distribution of the infrared rays radiated from the surface of the face including the inner corners of the eyes of the subject, and the estimation unit 102 obtains the temperature distribution from data of the light intensity distribution of the infrared rays, identifies the inner corners of the eyes from the obtained temperature distribution, and estimates the temperatures of the identified inner corners of the eyes as the body temperature.

Figure 3:
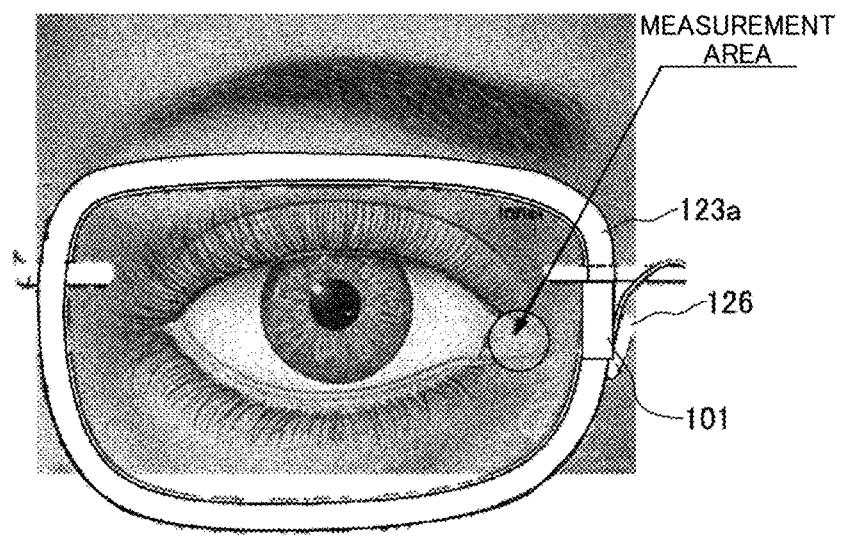
FIG. 3 is a configuration diagram showing a partial configuration of the body temperature estimation device according to an embodiment of the present invention.

For example, the estimation unit 102 identifies the inner corner of an eye from the highest temperature among the temperatures obtained from the measurement result of the infrared sensor 101 and estimates the body temperature of the subject. In the temperature distribution obtained by measuring the surface of the face including the inner corners of the eyes, the region having the highest temperature can be identified as the inner corner of an eye. For example, as shown in FIG. 3, by arranging the infrared sensor 101 on a rim 123a near a pad 126, the temperature of the inner corner of the eye can be acquired. The inner corner of an eye has a pink thin film called "semilunar fold" in the face. Since the semilunar folds are not covered by skin and have blood vessels running therethrough, the semilunar folds are considered to be a place where the internal temperature is most likely to be reflected when the surface temperature distribution of the face is measured. Therefore, the value of the body temperature can be obtained (estimated) by measuring the temperature of the inner corner of an eye.

The correction unit 103 corrects the body temperature estimated by the estimation unit 102 using the difference between the temperature of the inner corner of the left eye and the temperature of the inner corner of the right eye in the measurement result from the infrared sensor 101. As described above, for example, in the temperature distribution obtained by the measurement, the inner corners of the right and left eyes can be identified, and the temperature of each portion can be obtained. The estimated body temperature is corrected by the difference between the obtained temperature of the inner corner of the left eye and the obtained temperature of the inner corner of the right eye. For example, when there is a difference between the right and left temperatures, and when the temperature difference is equal to or less than a certain level, the higher temperature can be estimated as the body temperature. When the temperature difference between the right and left temperatures is equal to or greater than the certain level, it is considered a measurement error, and the temperature estimation by the estimation unit 102 is executed again. In this manner, an abnormal value of the measured temperature can be removed.

The estimation unit 102 and the correction unit 103 are each a microcomputer equipped with a CPU (Central Processing Unit), a main storage device, an external storage device, a network-connected device, and the like, wherein the CPU is operated (executes a program) by a program deployed in the main storage device to realize each of the functions described above. In addition, the respective functions can be distributed over a plurality of microcomputers.

The display control unit 104 displays the body temperature estimated by the estimation unit 102 on the display unit 105. For example, the display control unit 104 can display one value for the body temperature estimated by the estimation unit 102. The display control unit 104 can also display the temperature distribution of the body temperature measured by the infrared sensor 101. The display control unit 104 can display not only the body temperature but also data acquired from other sensors, not shown.

Figure 2:
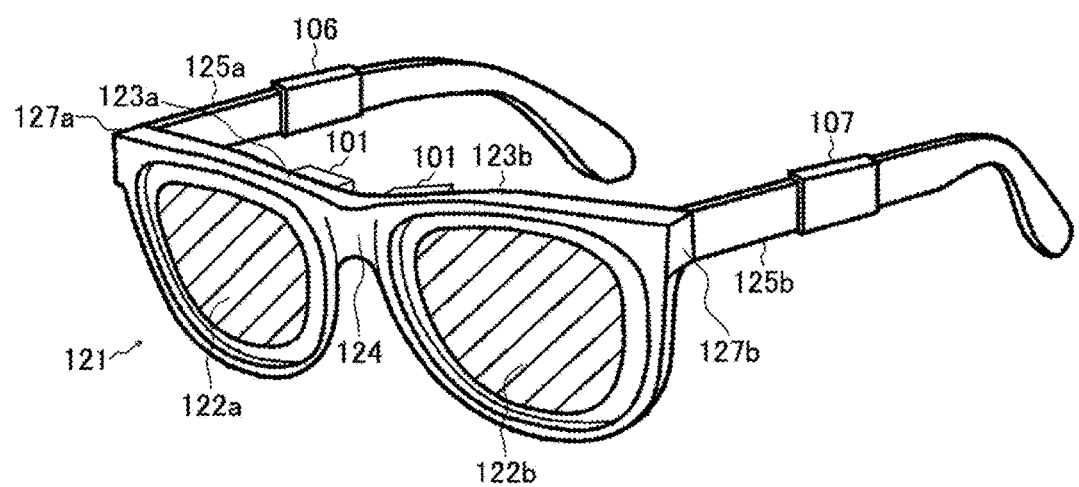
FIG. 2 is a perspective view showing a more detailed configuration of the body temperature estimation device according to an embodiment of the present invention.

As shown in FIG. 2, the holding mechanism 100 can be constituted by a spectacle frame 121. The infrared sensor 101 can be provided on, for example, the rim 123a and a rim 123b of the spectacle frame 121. For example, the infrared sensor 101 can be arranged on each of the rims 123a and 123b near a bridge 124. A lens 122a and a lens 122b of the spectacle frame 121 can be constituted of a transparent liquid crystal display device and used as the display units 105.

A temple 125a of the spectacle frame 121 can be provided (embedded) with a power source 106 for supplying power to the infrared sensor 101, the estimation unit 102, and the display control unit 104. The power source 106 may be composed of, for example, a secondary battery. The power source 106 also includes a switch for turning on/off the power to be supplied. Although the type, size, and arrangement of the switch are not limited, it is desirable to arrange the switch on a part of the spectacle frame 121 other than on the face side so as to be controlled easily even when worn by the wearer. A temple 125b can be provided (embedded) with an arithmetic processing unit 107 having the estimation unit 102, the display control unit 104, and the like.

Further, although not shown, the power source 106, power supply wiring to the lenses 122a and 122b composed of the arithmetic processing unit 107 and a transparent liquid crystal display device, signal wiring for connecting the infrared sensor 101 and the arithmetic processing unit 107, and the like are formed by connecting the temple 125a, the temple 125b, the rim 123a, the rim 123b, and the bridge 124.

In a case where the infrared sensor 101 is located in front of the face, it is desirable that the infrared sensor 101 and the body surface be apart from each other by a certain distance (in cm) for the safety of measurement of the radiated infrared rays. In a case where the infrared sensor 101 is provided on the front, it is not easy to take the distance described above, and there is a possibility of obstructing the view.

On the other hand, an armor 127a and an armor 127b that extend from the ends of the rim 123a and the rim 123b towards the pinna can be configured in such a manner that the infrared sensor 101 is arranged on the side surface side of the face and measurement can be performed obliquely with respect to the face, so that a distance can be provided between the infrared sensor 101 and the inner corners of the eyes, thereby acquiring an accurate temperature. However, the temperatures of the inner corners of the eyes cannot be obtained depending on the arrangement of the infrared sensor 101. The infrared sensor can also be arranged in each of the right and left armors 127a and 127b.

For example, if the infrared sensor is arranged too close to the tips, the positions of the inner corners of the eyes become outside of the measurement area. The temperature distributions around the edges of the eyes are measured. In this case, the part with the highest temperature is the edge of the eye. On the other hand, if the infrared sensor is arranged at a position close to the boundary between the armors 127 and 127b and the rims 123a and 123b, the temperature distributions of the region including the inner corners of the eyes can be measured.

Figure 4:
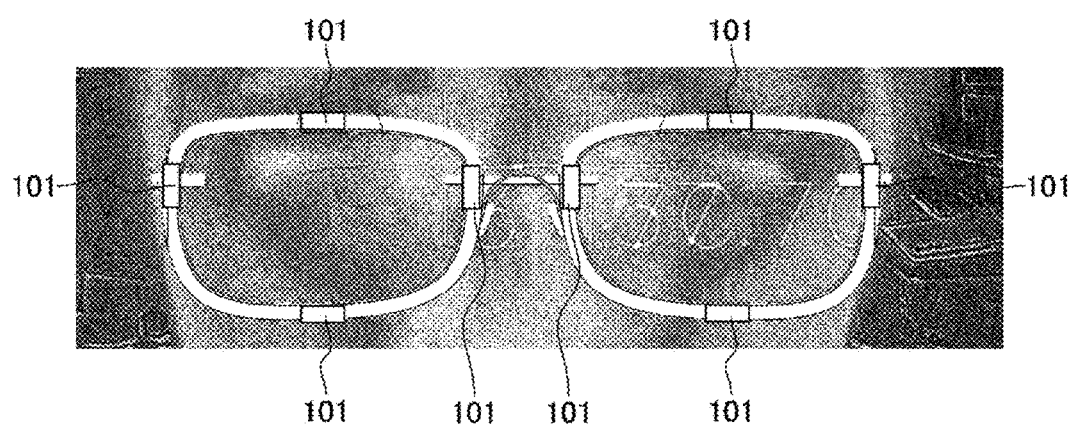
FIG. 4 is an explanatory view for explaining a partial configuration of the body temperature estimation device according to an embodiment of the present invention along with a measured temperature distribution.

As shown in FIG. 4, a plurality of infrared sensors 101 may be provided on the right and left rims of the spectacle frame, respectively. The estimation unit 102 estimates the body temperature of the subject by using the measurement results of the plurality of infrared sensors 101. If the information on the positions of the plurality of infrared sensors 101 (position information) is set in the estimation unit 102, the temperature distribution of a fixed number of pixels can be obtained by matching the measurement results of the infrared sensors 101 with the position information. The inner corners of the eyes are identified from the temperature distribution obtained in this manner, and the body temperature of the subject is estimated from the temperatures of these parts. It is known that the body temperature is higher than the temperature of the body surface, and the temperature 37.7° C. of the position of the inner corner of the eye having the highest temperature in the temperature distribution is estimated as the body temperature of the subject.

Figure 5:
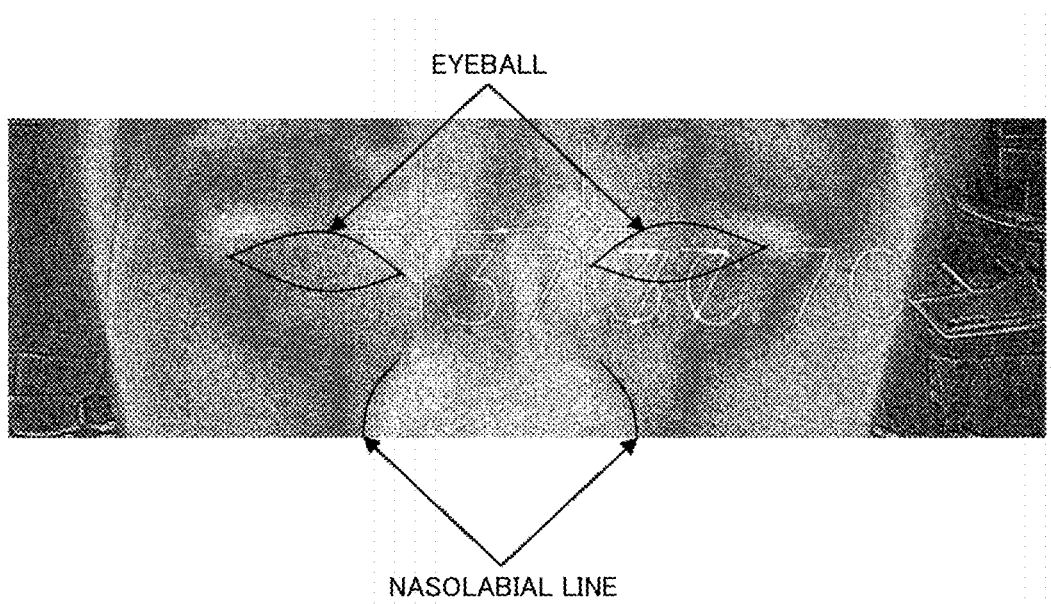
FIG. 5 is an explanatory view for explaining a state in which temperature gradients are formed at the nasolabial lines and the boundary between an eyeball and an eyelid in the temperature distribution obtained by the measurement.

The estimation unit 102 can identify the inner corners of the eyes by identifying the positions of the eyeballs from temperature gradients obtained from the measurement results of the infrared sensors 101. For example, as shown in FIG. 5, in the temperature distribution obtained by the measurement, a temperature gradient is formed at the boundary between a nasolabial line or eyeball and an eyelid. Therefore, the estimation unit 102 can identify the positions of the eyeballs from the temperature gradient (thermal image) in the temperature distribution obtained by the measurement using well-known image processing or the like. Once the positions of the eyeballs can be identified in this manner, the positions of the inner corners of the eyes can be identified.

The estimation unit 102 can also identify the inner corners of the eyes by identifying the positions of the eyeballs from temporal changes in temperature obtained from the measurement results of the infrared sensors 101. For example, the eyes periodically blink, and the temperatures of the eyelids are higher than the temperatures of the eyeballs. Therefore, the temperatures measured at the positions of the eyeballs periodically change. Therefore, the positions of the eyeballs can be identified from periodic temporal changes in temperature obtained from the measurement results of the infrared sensors 101. Once the positions of the eyeballs can be identified in this manner, the positions of the inner corners of the eyes can be identified.

Further, as described above, once the positions of the inner corners of the eyes, the nose, and the like are obtained, the deviation in wearing the holding mechanism 100 (spectacle frame 121) which is caused due to life activities and movements can be corrected by the estimation unit 102 in the measured temperature distribution.

A sensor for identifying the positions of the eyeballs can also be provided. In this case, the estimation unit 102 can identify the inner corners of the eyes from the positions of the eyeballs identified by the sensor and estimate the body temperature of the subject. The sensor may be, for example, a photosensor or a myoelectric sensor. For example, a photosensor is arranged on a temple of a spectacle frame or the like, and the reflection of the eyeball parts is measured. The eyes periodically blink, so the eyeballs and the eyelids have different reflectances. Therefore, the positions of the eyeballs, the timing and number of blinks, and the like can be measured from blinks measured by the reflection measurement. The amount of tears and sweat on the face of the subject can be measured by reflection. By comparing the eyeball positions based on the measurement results with the eyeball positions obtained from the temperature distributions, the estimation unit 102 can obtain more accurate positions of the inner corners of the eyes.

Figure 6:
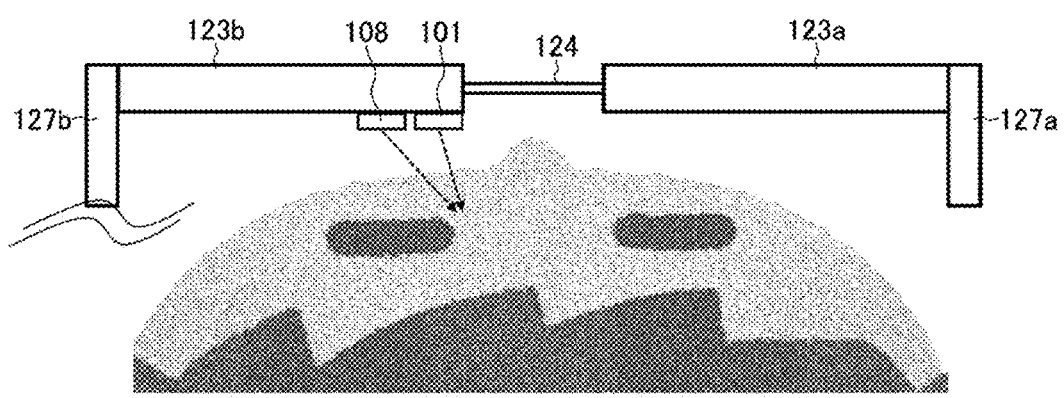
FIG. 6 is a configuration diagram showing a partial configuration of another body temperature estimation device according to an embodiment of the present invention.

As shown in FIG. 6, a position detecting unit 108 for detecting a portion where the infrared sensor 101 measures the temperature (infrared rays) and presenting the detected position can be further provided. The position detecting unit 108 can be constituted of a small camera and a laser pointer. For example, in a case where the infrared sensor 101 is provided on the rim 123b, the position detection unit 108 can be arranged in the vicinity of the place in the rim 123b where the infrared sensor 101 is installed.

The position detection unit 108 determines in which region the temperature is acquired by the camera and points to the determined region by the laser pointer. In addition, the determined area can be pointed to in a tactile manner by using a wind, vibration, or the like. The method for detecting the region where the temperature is measured and the method for presenting the detection result are not limited.

As described above, according to embodiments of the present invention, the infrared sensor for measuring infrared rays emitted from the surface of the face of the subject is provided in the holding mechanism, the body temperature of the subject is estimated from the temperatures of the inner corners of the eyes in the measurement result, and the estimation result is corrected by the difference between the temperature of the inner corner of the left eye and the temperature of the inner corner of the right eye. Therefore, even in a situation where the line of flow is not fixed, changes in the body temperature of the subject can be measured more accurately. By measuring the body temperature using a so-called wearable sensor having the holding mechanism, changes in the body temperature of a subject can be measured even in a situation where the line of flow is not fixed. In a configuration in which the temperature sensor is in contact, it is conceivable that psychological discomfort occurs due to a decrease in air permeability of the contact part and the feel of the sensor against the skin, possibly causing eczema in some people. On the other hand, the aforementioned problems do not occur by using the infrared sensor to measure the surface temperature of the face in a non-contact manner.

Also, it is apparent that embodiments of the present invention are not limited to the embodiments described above, and many modifications and combinations can be carried out by those having ordinary knowledge in the art within the technical idea of the present invention.

REFERENCE SIGNS LIST

100 Holding mechanism
101 Infrared sensor
102 Estimation unit
103 Correction unit
104 Display control unit
105 Display unit

The invention claimed is:

1. A body temperature estimation device, the device comprising:
   a holding mechanism configured to be mounted on a head of a subject;
   an infrared sensor provided in the holding mechanism and configured to two-dimensionally measure a distribution of infrared rays emitted from a surface of a face of the subject including an inner corner of a left eye and an inner corner of a right eye of the subject;
   an estimation circuit configured to estimate a body temperature of the subject from temperatures of the inner corners of the left and right eyes based on measurement results from the infrared sensor;
   a correction circuit configured to correct the body temperature estimated by the estimation circuit based on a difference between a first temperature of the inner corner of the left eye of the subject and a second temperature of the inner corner of the right eye of the subject based on the measurement results from the infrared sensor; and
   a display control circuit configured to display the body temperature corrected by the correction circuit on a display device,
   wherein the estimation circuit is configured to identify the inner corners of the left and right eyes by identifying positions of eyeballs of the subject from temporal changes of the temperatures obtained from the measurement results of the infrared sensor to estimate the body temperature of the subject.

2. The device according to claim 1, wherein:
   the holding mechanism comprises a spectacle frame;
   the infrared sensor is provided in the spectacle frame; and
   the display device comprises a lens of the spectacle frame.

3. The device according to claim 2, wherein:
   the spectacle frame comprises a frame, the lens, a pair of rims, and a pair of endpieces; and
   the infrared sensor is provided on a rim of the pair of rims or an endpiece of the pair of endpieces of the spectacle frame.

4. The device according to claim 2, wherein:
   the spectacle frame comprises a frame, the lens, a pair of rims, and a pair of endpieces; and
   the infrared sensor includes a first infrared sensor and a second infrared sensor, one of which is provided on each one of the pair of endpieces.

5. A pair of spectacles comprising:
   a spectacle frame configured to be mounted on a head of a subject, the spectacle frame comprising a frame, a lens, a pair of rims, and a pair of endpieces;
   an infrared sensor provided in the spectacle frame and configured to two-dimensionally measure a distribution of infrared rays emitted from a surface of a face of the subject including an inner corner of a left eye and an inner corner of a right eye of the subject;
   an estimation circuit configured to estimate a body temperature of the subject from temperatures of the inner corners of the left and right eyes based on measurement results from the infrared sensor;
   a correction circuit configured to correct the body temperature estimated by the estimation circuit based on a difference between a first temperature of the inner corner of the left eye of the subject and a second temperature of the inner corner of the right eye of the subject based on the measurement results from the infrared sensor; and
   a display control circuit configured to display the body temperature corrected by the correction circuit on the lens of the spectacle frame,
   wherein the estimation circuit is configured to identify the inner corners of the left and right eyes by identifying positions of eyeballs of the subject from temporal changes of the temperatures obtained from the measurement results of the infrared sensor to estimate the body temperature of the subject.

6. The pair of spectacles according to claim 5, wherein the infrared sensor is provided on a rim of the pair of rims or an endpiece of the pair of endpieces of the spectacle frame.

7. The pair of spectacles according to claim 5, wherein the infrared sensor includes a first infrared sensor and a second infrared sensor, one of which is provided on each one of the pair of endpieces.

* * * * *